United States Patent [19]
Bentley et al.

[11] Patent Number: 6,153,409
[45] Date of Patent: Nov. 28, 2000

[54] PROCESS FOR CONTINUOUS OPTIMIZED PROTEIN PRODUCTION IN INSECT LARVAE

[75] Inventors: William E. Bentley, Silver Spring; Hyung Joon Cha, Greenebelt; Minh Quan Pham, Rockville, all of Md.

[73] Assignee: University of Maryland Biotechnology Institute, Baltimore, Md.

[21] Appl. No.: 08/927,804

[22] Filed: Sep. 11, 1997

[51] Int. Cl.$^7$ .............................. C12P 21/06; C12P 21/04
[52] U.S. Cl. .................... 435/69.7; 435/69.6; 435/65.52; 435/69.1
[58] Field of Search ............................... 435/69.52, 69.7, 435/71.1; 800/4, 13

[56] References Cited

U.S. PATENT DOCUMENTS

| | | | |
|---|---|---|---|
| 5,427,858 | 6/1995 | Attie | 428/421 |
| 5,491,084 | 2/1996 | Chalfie | 435/189 |

OTHER PUBLICATIONS

Kuhn S and Zipfel PF. The baculovirus expression vector pBSV–His directs secretion of histidine–tagged proteins. Gene 162: 225–229, 1995.

Chao Y, Chen S, Li C. Pest control by fluorescence. Nature 380:396–397, Apr. 1996.

Bei R, Schlom J, and Kashmiri SVS. Baculovirus expression of a functional single–chain immunoglobulin and its IL–2 fusion protein. Journal of Immunological Methods 186:245–255, 1995.

Matsumoto T, Gargosky SE, Kelley K and Rosenfeld RG. Characterization of an insulin–like growth factor binding protein–5 protease produced by rat articular chondrocytes and a neuroblastoma cell line. Growth Regulation 6:185–190, Sep. 1996.

Chalfie et al., "Green Fluorescent Protein as Marker for Gene Expression", Science, 263:802–806 (1994).

Eriksson et al., "Green Fluorescent protein as tool for screening recombinant baculovirus", J. Virological Meth., 59:127–133 (1996).

Matsumura et al., "DNA shuffling brightens prospects for GFP", Nature Biotech, 14:366 (1996).

Miyajima et al., "Use of silkworm, *Bombyx mori* and an insect baculovirus vector for high level expression and secretion of biologically active mouse interleukin–3", Gene, 58:273–281 (1987).

Medin et al., "Efficient, low cost protein factories: Expression of human adenosine aminase in baculovirus infected insect larvae", PNAS, 87:2760–2764 (1990).

Niedz et al., "Green Fluorescent protein: An in vivo reporter of plant gene expression", Plant Cell Reports, 14:403–406 (1995).

Oker–Blom et al., "Highly efficient production of GFP and its derivatives in insect cells for visual in vitro applications", FEBS Lett., 389:238–243 (1996).

Pines et al., "GFP in mammalian cells", Trends Genet., 11(8):326–327 (1995).

Yeh et al., "Green Fluorescent protein as vital marker and reporter of gene expression in Drosophila", PNAS, 92:7036–7040 (1995).

*Primary Examiner*—Jasemine Chambers
*Assistant Examiner*—Ram Shukla
*Attorney, Agent, or Firm*—Carmen Pili Curtis

[57] ABSTRACT

The present invention provides for a recombinant insect larvae and a process of manufacturing proteins utilizing insect larvae that allows for the selection of individual larvae for harvest at the point of their optimal expression of a protein of interest. This invention also provides for a process to manufacture proteins in larvae that does not require synchronization of the infection, growth and harvest larvae to optimally manufacture a protein of interest. The invention further provides for a process of producing interleukin-2 in larvae.

17 Claims, 5 Drawing Sheets

PROCESS FOR CONTINUOUS OPTIMIZED PROTEIN PRODUCTION IN INSECT LARVAE

The application is under a government grant NSF BES 9319366 and a government contract Army DAAM01 96 C0037.

FIELD OF INVENTION

The present invention relates to a recombinant insect larva and the process of manufacturing proteins utilizing insect larvae, particularly *Trichoplusia ni* that allows for the selection of individual larvae for harvest at the point of their optimal expression of a protein of interest. The invention further provides for a process of producing interleukin-2 in larvae.

BACKGROUND OF INVENTION

Due to the advances of recombinant DNA technology, proteins that were normally produced in small quantities by organisms in nature and or were difficult to purify from such organisms can now be produced in large amounts. Typically, the gene which causes the proteins to be made in nature is inserted into the DNA of bacterial, yeast or mammalian cells; the cells cultured; and the protein purified from the cells after sufficient growth.

However, the nature of the cells used to produce the protein of interest (subject protein) can limit their application or require expensive equipment and reagents. For example, proteins expressed by higher organisms often undergo modifications after they are initially expressed by the cells. Such modifications are referred to as glycosylation. Glycosylation of proteins produced in the cells of mammals and other higher organisms in nature is often necessary for such proteins to elicit biological activity.

However, bacterial cells are incapable of glycosylating proteins. Consequently, they often cannot be used to make proteins which are intended to elicit biological activity in mammals, fish, and insects.

Although mammalian and insect cell systems can be used to manufacture glycosylated proteins, expensive and complex media are required and the bioreactors, in which the cells are grown, must be run for extended periods creating a risk of contamination of the cell culture.

Because insect larvae can be grown quickly and inexpensively, there have been attempts to genetically engineer them to express a subject protein instead of using cells to produce a subject protein. The fact that yields can be obtained from insect larvae which cannot be obtained from bacterial cells also makes them an appealing alternative to cell based protein manufacturing.

An additional reason for utilizing insect larvae is that a system is available which can readily be used to genetically engineer them. Baculoviruses characteristically have a circular double-stranded DNA genome which is contained in a rod-shaped enveloped virion. The DNA can be manipulated to incorporate a gene which encodes a subject protein. Like all viruses, the DNA of the baculovirus will cause the cells of its host to produce the proteins encoded in its DNA. Consequently, if the DNA of a baculovirus is manipulated to incorporate a gene which codes for a subject protein and that baculovirus allowed to infect an insect larvae, the cells of that larvae will produce the subject protein.

Attie et al., U.S. Pat. No. 5,472,858 disclosed this approach with the tobacco hornworm. After the hornworm is infected with a recombinant baculovirus, it begins secreting the recombinant protein into its hemolymph. The hemolymph can then be withdrawn using a syringe throughout the larvae's growth.

However, there is a drawback to this specific method. Although the tobacco hornworm larvae is ideal for the physical manipulation because of its large size, a great deal of manual labor is required to extract the recombinant protein if large numbers are to be cultivated.

Furthermore, in this method, the individual larvae are injected with baculovirus to initiate infection, which can also be labor intensive.

Besides this problem, many larvae produce cellular and digestive proteases when they overexpress genes, as in the case of recombinant engineering with baculoviruses. It is the function of proteases to break down various proteins in the larvae. As a result of the expression of these proteases, the subject protein could be consumed while in the larvae.

Additionally, in many insect species, recombinant proteins cannot be recovered from the larvae after a certain point because the baculovirus eventually kills its insect host. In the larvae of *Trichoplusia ni*, more commonly referred to as the cabbage looper, the larvae die after five to seven days after infection with the baculovirus and melanization occurs. During melanization, many of the proteins condense into a dark, gluey mass from which recovery of the recombinant protein is impossible.

Thus, the harvest of the larvae currently has to be synchronized with the viral infection cycle and their life cycles to obtain an optimal yield. However, all the larvae in a population will not have the same rate of growth and viral infection since characteristics, such as individual growth rates, can vary widely among a population. Consequently, although all of the larvae in a production population may have been infected with baculovirus at the same time, some will not have attained their optimal level of protein expression when the entire population is harvested simultaneously.

Sacrifice and assay of individuals within the population of a production run might be a method to determine when most of the larvae have obtained the optimal expression of the subject protein. However, due to random variations of individual characteristics in a population, the individuals selected may not be representative of the entire population. Large samplings may result in a more accurate profile of expression with the population, but this is time consuming and labor intensive and will leave less larvae for harvest.

Moreover, this "batch" run method, where larvae are synchronously infected and harvested, requires an entirely new run to be started to make up for any deficiencies in yield that become apparent from an existing production run. That is, if a "batch" run is showing signs of a poor yield, adding more larvae would be impractical since their infection cycles will not be synchronized with those of the already infected larvae. The result being that the optimal level of protein expression in the new larvae will not be obtained when the entire population is harvested.

The preferred alternative to the "batch" run approach is a "continuous" approach where larvae can be continually added to and harvested from a production population regardless of the stage of infection or growth of other larvae in the population.

From the above, there is a need for an insect larval protein manufacturing system that allows easy selection of individual larvae for harvest at their optimal point of protein expression with minimal labor that does not require synchronous infection and harvest.

SUMMARY OF THE INVENTION

The present invention is directed toward the need for a semi-continuous or continuous process for protein manufacturing with insect larvae which does not require synchronization of infection, growth and harvest and permits individual larvae to be easily selected for harvest at the point when they are optimally expressing a subject protein. A system for protein manufacturing in insect larvae having features of the present invention comprises introducing a gene that encodes a subject protein into the cells of an insect larvae; introducing a second gene, known as a reporter gene that will simultaneously express a protein, hereafter referred to as a reporter protein, to indicate the expression of the first gene, such indication being a characteristic that affects the appearance of the living larvae; monitoring the larvae for expression of the gene encoding the subject protein through the production of reporter protein and protein of interest, harvesting the larvae and recovering the protein of interest.

It is an advantage of the present invention that a low cost "continuous" system is described for the optimized production of a subject protein, which permits larvae to be continuously added to and harvested from a single production run.

It is an advantage of the present invention that a low cost system is described for the optimized production of a subject protein in insect larvae that permits individual larvae to be harvested based upon their expression of a subject protein thereby insuring that all the larvae of a production population optimally express a subject protein when harvested.

It is an advantage of the present invention that because indirect detection of the subject protein in the individual larvae facilitates their selective harvest, it is not required to synchronously infect, cultivate and harvest the larvae.

It is an object of the present invention to provide for a process for the production of a subject protein in insect larvae of the species *Trichoplusia ni*.

It is an object of the present invention to link the gene encoding the subject protein with the reporter gene so that the subject protein is expressed as a fusion protein with the reporter protein.

It is an advantage of the present invention that the actual amount of a subject protein in individual larvae of a production population can be determined by measuring the intensity of expression of a reporter gene that is linked to the gene encoding a subject protein.

It is a further advantage of the present invention that a more accurate determination of the level of expression of a subject protein in larvae of a production population is permitted which does not require sacrificing larvae, thus leaving more for harvest.

It is a further advantage of the present invention that a subject protein does not have to be attempted to be extracted and purified from all of the larvae of a production population to determine if a production run was successful, thus avoiding unnecessary protein extraction and purification.

It is a further advantage of the present invention that the physical handling and manipulation of each individual larva in a production population is not required to extract a subject protein thereby reducing the amount of labor and time expended in extracting the subject protein from the larvae.

It is a further object of the present invention to link the reporter gene and the gene encoding the subject protein via a gene which expresses a protein that can be cleaved by a specific enzyme.

It is an even further object of the present invention to link the reporter gene and the gene encoding the subject protein via a gene which expresses a protein that can be cleaved by enterokinase.

It is an advantage of the present invention that the subject protein and the reporter gene can be easily separated and purified when expressed as a fusion protein.

It is an object of the present invention that a histidine affinity tail is engineered onto the reporter protein.

It is an advantage of the present invention that a fusion protein formed by the subject protein and the reporter protein can be easily separated from a homogenate by binding a histidine affinity tail that is engineered onto the reporter protein.

It is a further object of the present invention that the gene encoding the subject protein expresses interleukin-II.

It is an advantage of the present invention that a system is described in which permits the low cost and efficient production of interleukin-II.

It is a further object of the present invention that the gene for the green fluorescent protein is used as the reporter gene.

It is an advantage of the present invention in that a system is described in which individual living larvae are selected for harvest according to the larvae's green color in normal light or glow in other wavelengths of light as a low cost and efficient means to select individual larvae for harvest.

BRIEF DESCRIPTION OF THE DRAWINGS

FIG. 2B SDS-PAGE (left) and Western blot (right) analysis of GFPuv. Molecular weight markers (lane M) are indicated on the left-hand side of the gel. Lane 1 is day 4 uninfected larvae, lane 2 is 2 day post-infection larvae, lane 3 is 3 day post-infection larvae, and lane 4 is 4 day post-infection larvae. Lanes 5 to 7 are standard purified wild-type GFP of 0.1, 0.3, and 0.6 $\mu$g, respectively, for quantification purposes. The position of GFPuv is indicated on the right-hand side of the gel.

DESCRIPTION OF THE INVENTION

In accordance with the present invention, the expression and amount of a subject protein in an insect larvae is indicated by the simultaneous expression of a reporter gene which can be visualized in living insect larvae so that they can be selectively harvested in a manufacturing process. The subject protein could be any protein that is capable of expression in insect larvae. Such expression has been successfully performed with interleukin-II (Cha et al., in print; Pham et al., submitted for publication), α-interferon (Maeda et al., 1995), polyhydrin-IGF fusion protein (Marumoto et al., 1987), mouse interleukin-3 (Miyajima et al., 1987), luciferase (Palhan et al.), influenza virus hemaglutin (Juroda et al., 1989), human adenosine deaminase (Medin et al., 1990) and human group II phospholipase $A_2$.

Since there are reports that glycosylation patterns in insect larvae are superior to those in insect cells and much closer to human patterns, proteins which require glycosylation to elicit biological activity are ideal candidates for use in the present invention. (Davis and Wood, 1995), (Page and Maizels, 1992).

By their common definition, "reporter genes" are genes that express a protein, a reporter protein, which causes some determinable characteristic in a recombinant system simultaneously with the expression of another gene to indicate the expression of that other gene. Consequently, the reporter gene of the present invention is capable of expression in insect larvae at the same time as the gene encoding the subject protein. The determinable characteristic is a change in appearance of the living larvae that can be easily visualized. Ideally, the characteristic is visible in normal light or other wavelengths of light. Thus, determination of the reporter gene's expression is simply accomplished by viewing the larvae under normal light conditions and other light conditions.

Preferably, the reporter protein is highly stable since stability of such protein is thought to contribute to the level of expression of the gene for the subject protein (Cha et al., 1997). This has been the case in a few examples in bacterial (Pham et al., submitted), (Pilon et al., 1997; Pilon et al., 1997). In this particular case, a gene for a protein known for its instability was fused with a gene known for its instability. The resultant fusion protein had the stability characteristics of the more stable of the component subunits.

To add a capability of quantitative indication to the reporter gene in the present invention, the gene for the subject protein and the reporter gene can be linked so that the subject protein can be expressed as a fusion product with the reporter protein. In this embodiment, the actual amount of subject protein produced in an insect larvae will be directly related to the amount of reporter protein produced.

This refinement is also significant because it will permit the reporter gene not only to indicate the level of gene expression of the subject protein, but also its actual amount in each larvae. This is preferred for three reasons. First, it is possible that the subject protein could be degraded by proteases expressed by the larvae due to overexpression. Overexpression is caused by recombinant engineering with baculovirus or may be expressed as a natural consequence of the larval cycle. As a result, although the expression of the reporter gene may indicate the expression of the desired gene, it may not reflect the actual amount of subject protein present in larva.

By linking the gene for the subject protein with the reporter gene to express a fusion product, it is more likely that activities in the larvae which affect the subject protein will affect the reporter protein. Thus, expression of the reporter gene will indicate the actual presence of the subject protein in the larvae rather than only its expression.

The second reason why it is preferable to link the reporter gene and the gene for the subject protein is because the amount of one will directly correspond to the amount of the other in the larvae. Consequently, the intensity of the effect created in the appearance of the living larvae by the amount of reporter protein in the larvae can be used to directly measure the amount of subject protein actually present in each larvae.

Third, harvesting and purification of the subject protein can be simplified by expressing the subject protein as a fusion protein and the reporter protein. In such an embodiment, an affinity ligand could be engineered onto the reporter protein. The affinity ligand can be used to bind and separate fusion protein from the larval extract during the initial purification.

As a further means to simply purification, the linkage between the gene for the subject protein and the reporter gene could comprise a gene which expresses a protein that is cleaved by a specific enzyme. Once the fusion product is separated from the homogenate via the affinity ligand, it could be exposed to the enzyme which cleaves the linking protein to separate the subject protein and the reporter protein. Then, a one step purification could be performed to purify the subject protein.

Because the presence of the reporter protein can be easily visualized, linkage of the reporter gene and the gene encoding the subject protein will permit the progress of the subject protein to be monitored through the purification process directly and indirectly. This will also serve to facilitate purification.

The gene for the green fluorescent protein (GFP) is an excellent choice for the role of reporter gene. GFP was originally isolated from the jellyfish, *Aequorea victoria,* and was first described in 1962 (Shimomura et al., 1962). GFP emits bright green light when simply exposed to UV or blue light, unlike other bioluminescent reporters. The emission of green light is due to the transfer of energy from the photoprotein, aequorin, of the organism to GFP (Johnson et al., 1962). The cDNA of GFP was cloned from *Aequorea victoria* in 1992 (Prasher et al., 1992). GFP is a 238 amino acid protein with a molecular weight of 28 kDa (Chalfie et al., 1994) and has a major absorption peak at 395 nm and a minor peak at 470 nm with a single emission peak at 509 nm (Chalfie et. al., 1994). Advantageously, its fluorescence is species-independent and requires no substrate, cofactor, or additional proteins for illuminating green light. GFP has been successfully expressed in several host organisms and cells such as *E. coli* (Chalfie et al., 1994, Crameri et al., 1996), yeast (Stearns, 1995; Schlendstedt et al., 1995), mammalian cells (Kain et al., 1995; Pines, 1995; Ikawa et al., 1995; Wu et al., 1995; Crameri et al., 1996), insect cells (*Spodoptera frugiperda,* Sf-9) (Reilander et al., 1996), and plant cells (Niedz et al., 1995; Heinlein et al., 1995). Unlike other reporter tags such as luciferase, b-galactosidase, or fluorescent-tagged antibodies, GFP does not require fixation techniques that are toxic to the cells under the investigation (Chalfie et al., 1994).

GFP mutations have also been developed that serve well in the capacity of the reporter gene. GFPuv was optimized for UV excitation (Crameri et al., 1996). GFPuv is 18 times brighter than wild-type GFP and can be easily detected by the naked eye when excited with standard, long-wave UV light (e.g., source for many DNA transilluminator light tables). This variant contains additional amino acid mutations which increases its translational efficiency. Purified GFPuv has the same excitation and emission maxima as wild-type GFP. GFPuv expressed in E. coli is a soluble, fluorescent protein even under conditions in which the majority of wild-type GFP is expressed in a nonfluorescent form agglomerated into inclusion bodies (Crameri et al., 1996).

Mutants of GFP are available commercially and include variants with the blue and red-shifted proteins along with several that have various intensities of green for which the codon composition has been altered. Among the commercial vendors of these mutants are Life Technologies, Inc., Clontech, Inc., and Invitrogen, Inc.

Introduction of the gene encoding the subject protein and the reporter gene as envisioned in the present invention is ideally effected via Autographica californica Nuclear Polyhedrosis Virus (AcNPV) or Bombyx mori Nuclear Polyhedrosis Virus (BmNPV), which are both baculoviruses that infect only insects. Baculoviruses that can be manipulated to incorporate DNA from other sources are available commercially. Construction of appropriate baculovirus vectors to express a subject protein and reporter gene is apparent to one skilled in the art. However, the following text which is incorporated herein by reference is an example of a reference that provides sufficient information and instruction to enable construction of a suitable baculovirus vector: Baculovirus Expression Vectors: A Laboratory Manual by D. R. O'Reilly, L. K. Miller and V. A. Lucklow (W. H. Freeman and Co., New York, N.Y., 1992).

There are also commercial kits available that provide the necessary instructions and reagents for baculovirus vector construction.

The expression level of the subject protein may be increased by the use of polyhedrin negative baculovirus. In this virus, the gene encoding the subject protein may be put under the polyhedrin promoter which may help boost the expression level when compared to the p10 promoter. According to a recent study, the AcNPV's infectivity will not be significantly reduced if it lacks a polyhedra (van del Heuvel et al., 1993).

However, a polyhedra is required for efficient oral infection (Pham et al., 1997). To effect oral infection once a baculovirus has been engineered appropriately, a solution containing the baculovirus is sprayed on the larvae's food or allowed to soak into it.

Other methods of infection, such as injection of the baculovirus into the hemocoel of the larvae, can be utilized, however, they may be more labor intensive.

Because foreign proteins have been expressed in a variety of insect larvae; Bombyx mori, the silkworm (Maeda et al., 1985; Miyajima, et al., 1987), Trichoplusia ni, the cabbage looper larvae (Medin et al., 1990) and Manduca sexta, the tobacco hornworm (U.S. Pat. No. 5,471,858) there is a wide selection of insect larvae that could be utilized with this system. The larvae of the cabbage looper has been utilized and is typical of the ideal larvae envisioned for use in the present invention. Although it is known that the BmNPV vectors will work equally well. Cabbage looper larvae can be ordered from commercial sources such as Entopath, Inc. (Easton, Pa.) and can be easily grown in a laboratory according to the instructions provided by the supplier. Media for the larvae can be made from alfalfa meal, pinto beans, Brewer's yeast, ascorbic acid, wheat germ, sorbic acid, vitamins, and antibiotics (aureomycin).

There is a balance to be struck as to the best stage in the larval cycle of the cabbage looper to initiate baculovirus infection. The baculovirus kills the larvae after five days so there is a limited time in which they have to grow and express the subject protein. Because the size of the larvae is related to the amount of protein they express; small larvae produce insignificant amounts of protein, it would be ideal to infect them when they are large. However, if the larvae are too large, too much baculovirus is required for infection. Baculovirus infection in the fourth instar, which is the last instar prior to pupation, seems to strike the optimal balance between the larvae's size and the amount of virus required for infection.

Additional measures may be utilized to enhance baculovirus infection of the cabbage looper larvae and thereby increase the protein yield. It has been observed that co-infection of cabbage looper larvae with a Trichoplusia ni GV (TnGV) can increase the infectivity of AcNPV (Tanada, 1989; Hukuhara et al., 1987), thus permitting smaller amounts of AcNPV to be used for infection. By lowering the amount of virus needed for infection, the propagation of the virus can be delayed so that the peak of protein expression does not coincide with peak protease activity (Pham et al., 1997).

A preferred embodiment of the present invention is a completely "continuous" protein manufacturing process. What is meant by a "continuous process" is that the larvae can be continually added to and harvested from a production population. This is in contrast to the traditional "batch" run approach in protein manufacturing in which a group of insect larvae would be infected with baculovirus at the same time, allowed to grow for the same period and then harvested at the same time. Because the "batch run" approach relies on adhering each larva to the same growth, baculovirus infection and harvest time schedule, rather than sorting the larvae by individual characteristics, the addition of more larvae is not practical because there is no way to determine which growth, baculovirus infection and harvest schedule the individual larvae are on.

The term "continuous process" refers to infecting an insect larvae by introducing a gene encoding the subject protein operatively linked to a protein reporter gene into an insect larvae; cultivating the larvae under suitable conditions for the expression of the gene encoding the subject protein and the protein reporter gene; monitoring the larvae for the expression of the gene encoding the subject protein through the production of reporter protein and a protein of interest; harvesting the larvae; and recovering the protein of interest.

The term "suitable condition" refers to conditions which allows the expression of the gene of interest and the reporter gene, particularly green fluorescent gene. The preferred conditions include infection with a viral loading of at least $5 \times 10^7$ pfu/mL recombinant baculovirus, temperature of at least about 30° C., harvesting of the larvae at least 3–5 days, more particularly at least 4 days, after post infection; at a pH of at least about 3.5 to about 4.0 and in the presence of protease inhibitors such as PMSF, EDTA and benzamidine, preferably at least about 1.5 mM to about 0.02%.

A semi-continuous embodiment is possible where larvae are all infected simultaneously, but then harvested individually when they express the reporter gene.

It is envisioned that the present invention will allow selective automated baculovirus infection of individual larvae. An automated infection system could be utilized by hatching cabbage looper eggs and automatically selecting fourth instar larvae based on size and/or weight, allowing them to feed and introducing them to a production population via a conveyor belt apparatus or some other means where infecting baculovirus has been spread on their food.

It is also envisioned that the present invention has an automated system for selecting individual larvae for harvest. A monitoring capability could be added to such a system by attaching an LED/detector to each fin where the larvae hang and wiring the LED/detector and a fin to a separate controller. When the LED/detector detects a sufficient intensity of the green color of the GFP expressed in a larva, a signal would be sent to the controller which in turn would deliver voltage to the fin where the transmitting LED/detector is located, The voltage would shock the larva causing it to fall off the fin into a collection receptacle.

Another possible monitoring system could resemble the conveyor belt/switching gate apparatus used by dairy egg manufacturers, where the brightest larvae are harvested.

Some aspects of a possible automated system are in use already. For example, a mass rearing system has been developed and patented by AgriVirion (Ithaca and NY, N.Y.), however, it was developed for mass production of the baculovirus and is not capable of monitoring individual larvae. In this system, the larvae crawl on the side of each finger (metal protrusion like a cooling fin) and eat the diet on the top of the unit. They are suspended so that excrement is dropped to the bottom.

Although an automated system is preferable, since GFP mutants expressed in larvae, such as GFPuv, can be discerned by the human eye in normal laboratory light in larvae at least two or three days after infection with baculovirus and detection of GFP with human eyesight under UV light possible after at least three days, manual infection and selection for harvest is certainly feasible.

Preservation of the larvae after selection for harvest in the present invention is envisioned to be conducted by freezing the selected larvae and then homogenizing the larvae in conditions which minimize the activity of proteases. Such conditions could consist of lowering the pH of the larvae homogenate. Proteases in insect larvae were observed to have the least activity at pH's of at least about 3.5 to about 4 (Pham et, al., 1997).

Cocktails of protease inhibitors can be combined with low pH's to minimize the effect of proteases even further. Phenylmethylsulphonylfuloride (PMSF) has been found to be an inhibitor of insect protease activity at lower molecular weights (Pham et. al., 1997).

Purification of the subject protein from the homogenate can be achieved with a number of methods, such as affinity chromatography. Purification with this method can be enhanced by engineering a fusion gene that includes a histidine affinity tail on the N-terminus of the reporter protein of the fusion protein. The homogenate can be exposed to a surface or matrix that binds the histidine affinity tail of the fusion protein. After the homogenate has been removed, the fusion protein can be removed by exposing the binding surface to conditions which favor dissociation of the histidine affinity tail.

Separation of the subject protein from the isolated fusion protein can be achieved by engineering linkage of the gene encoding the subject protein and the reporter protein with a gene that expresses a protein that is cleaved by a specific enzyme. Proteins cleaved by enterokinase have been found effective for providing a stable link to hold subject protein and the reporter protein together during purification from larval homogenate and also allowing easy cleavage of the subject protein from the fusion protein.

Once the subject protein is cleaved from the fusion protein, a one-step purification can be utilized to purify from the reaction.

The previously described versions of the present invention have many advantages including the easy selection of larvae -at the point of their optimal protein expression. Because the visible expression of GFP will occur simultaneously with the expression of the subject protein, each larvae can be selected for harvest when it is expressing the optimal amount of the subject protein. Furthermore, if the GFP is fused with the subject protein when expressed, it is possible in the present invention to quantify the amount of subject protein in an individual larvae. This in turn allows an estimation of the total yield from a production population to be made.

In addition, larvae which are not expressing significant amounts of the subject protein can be removed from the production population so that resources are not expended attempting to purify the subject protein from them.

Because the larvae can be grown on inexpensive media, it is unnecessary to incur the high expense of formulating complex media and maintaining bioreactors.

Another advantage of this invention is that continuous production runs instead of individual "batch" runs could be maintained. In such embodiments, the infection cycle of all larvae could be continuously infected and added to the same culture as previously infected larvae. This would permit the addition of larvae if a production population was exhibiting indications of a poor yield. The continuous approach to growing different insect larvae will be distinct from previous green fluorescent methods of producing different proteins of interest because the continuous method will be able to use the intensity of fluorescence in the selection of the larvae at the optimum stage in protein production. The optimum amount of fluorescence will permit one of ordinary skill in the art to select the larvae as they come to the point of maximum protein production and harvest these larvae. The linkage of infection by the green fluorescent protein and the protein of interest will increase the efficiency of production.

Another advantage of the present invention is that minimal manual labor is needed to extract the subject protein from the larvae because sufficient numbers of larvae can be preserved and accumulated to make large scale purification possible.

Because affinity ligands and cleavable proteins can be engineered onto the reporter gene, large scale purification of subject proteins is simplified when the present invention it utilized to manufacture them.

The expense of manual labor is also avoided by orally infecting the larvae rather than injecting baculovirus into their body cavities.

Example 1

This example describes the optimized production of interleukin in larvae of the cabbage looper, *Trichoplusia ni*. The eggs were obtained from a commercial supplier (Entopath, Inc., Easton, Pa.) and hatched in Styrofoam cups containing solid food (Entopath) at 30° C. A recombinant baculovirus, containing human IL-2 gene (IL-2) under p10 promoter was utilized as the gene for the subject protein. The sequence for IL-2 is publicly made available. (Kashima et al., 1985), (Tamiguchi et al., 1983)

The larvae were infected by spreading 500 µL recombinant baculovirus ($5 \times 10^7$ pfu/ML) on the media which was obtained pre-made in Styrofoam cups (Entopath). The cups were covered and allowed to stand an hour for the virus to be completely absorbed by the media. The fourth instar larvae (about 4 days after hatching) were then placed into the cups (approximately about 10 to 15 larvae per cup). The cups were then inverted and the larvae were allowed to feed on the infected food at 30° C. The fecal matter dropped onto the lid so it could be discarded daily.

The infected larvae were then collected and frozen at −60° C. until they were ready for recombinant protein, total protein, and protease assays. The frozen larvae were thawed, and homogenized in phosphate buffered saline (PBS) containing 60 mM dithiothreitol (DTT), and 0.5% Triton X-100 at pH 7.0. The samples prepared for recombinant protein assay also contained the following protease inhibitors: 0.02% (w/v) PMSF, 1 mM EDTA, and 0.2 mg/mL benzamidine. We had previously determined that this cocktail of protease inhibitors was effective in minimizing proteolysis in the extract steps (unpublished results). The homogenate was then centrifuged at 4° C. to remove large debris. After centrifugation, the supernatant was also further clarified with using a 0.22 micron filter.

GFP and IL-2 Assay

The GFP assay was performed by measuring fluorescence intensity using a fluorescence spectrometer (LS-3B; Perkin-Elmer Ltd., Beaconsfield, Buckinghamshire, England) at an excitation of 395 nm and emission at 509 nm. The quantity of GFP was determined using pure recombinant GFP (Clontech) as a calibration standard on Western blots. The IL-2 assay was performed using an IL-2 assay kit (Cytoscreen™ immunoassay kit; BioSource International Inc., Camarillo, Calif.). This assay was a solid phase sandwich Enzyme Linked-Immuno-Sorbent Assay (ELISA). The kit contains microtiter strips coated with IL-2 with specific monoclonal antibody. Once the sample was pipetted into wells on the microtiter strips, the IL-2 was bound to the monoclonal antibody during incubation. After washing, a biotinylated polyclonal antibody specific for IL-2 was added. This antibody was bound to the IL-2 captured in the first incubation. After removal of the polyclonal antibody, an enzyme, streptavidin-peroxidase, was added which bound to the polyclonal antibody to complete a four-member sandwich. After incubation, the excess enzyme was washed off, and a substrate was added which produces a color change. The intensity of the color (read at 450 nm) was measured using a microplate reader (Dynex Technologies, Inc., Chantilly, Va.) and was directly proportional to the concentration of IL-2 in the original sample.

SDS-PAGE and Western Blot Analysis

The total protein assay was performed using a protein assay kit (Bio-Rad Lab., Hercules, Calif.) with bovine serum albumin as a standard. Sodium dodecyl sulfate-polyacrylamide gel electrophoresis (SDS-PAGE) (Laemmli, 1970) was performed by mixing the sample with sample buffer (0.5 M Tris-HCl, pH 6.8, 10% glycerol, 5% SDS, 5% b-mercaptoethanol, 0.25% bromophenol blue), incubating at 100° C. for 3 min, centrifuging for 1 min, and loading onto a 15% slab gel. After electrophoresis, the gel was stained by Coomassie brilliant blue, or for Western blot, the gel was transferred onto a nitrocellulose membrane (Bio-Rad) with a Bio-Rad Mini-Trans Blot Cell in Bjerrum and Schafer-Nielsen transfer buffer (48 mM Tris, 39 mM glycine, and 20% methanol; pH 9.2) for 40 min at 20 V. The nitrocelluose membrane was probed with 1:12000 dilution of polyclonal anti-rGFP antibody (Clontech), and detected with 1:5000 dilution of goat anti-rabbit IgG conjugated to alkaline phosphatase (Kirkegaard and Perry Laboratories, Gaithersburg, Md.) and BCIP/NBT (5-bromo-4-chloro-3-indolyl phosphate/nitro blue tetrazolium) color development reagent (Sigma) (Becht et al., 1988). The stained membranes were photographed by a digital camera (Strategene Eagle Eye) capable of printing out and converting the image to a graphic picture file. The digitized image stored in the file was then analyzed by an NIH image software (NIH Image, written by Wayne Rasband at the U.S. National Institute of Health and available from the Internet by anonymous ftp from zippy.nimh.nih.gov). Pure GFP (Clontech) concentrations of 0.1, 0.3, and 0.6 μg were loaded from Western blot calibration.

SDS-Gelatin PAGE Protease Activity Assay

Cellular protease activity is monitored with a modification of the gel electrophoresis method (Harcum and Bentley, 1993). The frozen supernatant samples were thawed at 37° C. A mixture of 10 mL 10% SDS, 70 mL STOP solution (0.123 M Tris-HCl, 20% (w/v) glycerol, 0.25% bromophenol blue), and 20 mL cell sample were vortexed and incubated at 37° C. for 20 min. After incubation the samples were loaded into the wells of a slab polyacrylamide gel with SDS and gelatin copolymerized into the matrix. After 1 h at constant voltage (200 V), the gels were washed in 2.5% Triton X-100 for 1 h to remove SDS. The gels were then incubated at 37° C. for 24 h in an incubation solution (containing 100 mM glycine, 2 mM ATP, and 2 mM $MgCl_2$; pH 7.5) to regenerate protease activities. The gels were then stained for one hr in 0.2% amido black staining solution and destained in amido black destaining solution. Proteolytic activities were evident by clear bands that appear on the gel. The cleared zones were separated by relative molecular weight. The intensity of the cleared band was proportional to activity of the protease (Harcum and Bentley, 1993).

Spectrum of GFPuv in Infected Insect Larvae

Figure 1:
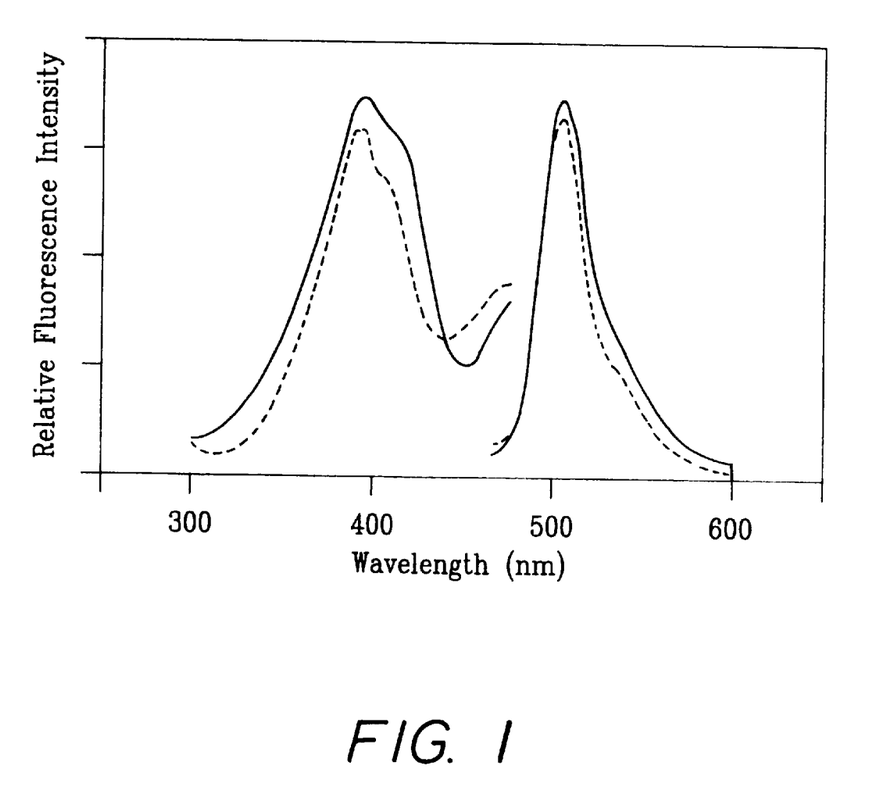
FIG. 1. Fluorescence excitation (left) and emission (right) spectra of insect larvae-generated GFPuv (solid lines) and pure recombinant wild-type GFP (dotted lines). Crude larvae protein solution was prepared by breaking larvae using a homogenizer, and pure wild-type GFP was purchased from Clontech. When recording the excitation spectrum, emission wavelength was set as 509 nm. Also, when recording the emission spectrum, excitation wavelength was set as 395 nm.

After infecting with the recombinant baculovirus, vGFPuv, fluorescent excitation and emission spectra of recombinant GFPuv from insect larvae were recorded on a fluorescence spectrophotometer. As presented in FIG. 1, the fluorescence excitation maximum of the larvae crude protein solution was at ~395 nm and the emission maximum was at ~509 nm. The observed maximum and the shape of the spectrum were virtually identical to those of purified recombinant wild-type GFP from E. coli (Inouye and Tsuji, 1994) as well as those described for native wild-type GFP (Bokman and Ward, 1981).

Visual Expression Profile of GFPuv

Time course larvae samples were placed, with uninfected control larvae, on a UV table (365 nm) and photographed. There was substantial growth in infected and uninfected larvae. Also, until 2 dpi, no fluorescence was seen. However, the 3 and 4 dpi larvae emitted bright green fluorescence upon UV excitation. Therefore, a clear and simple distinction was made between infected and uninfected larvae.

Quantification of GFPuv Expression Profile

Figure 2A:
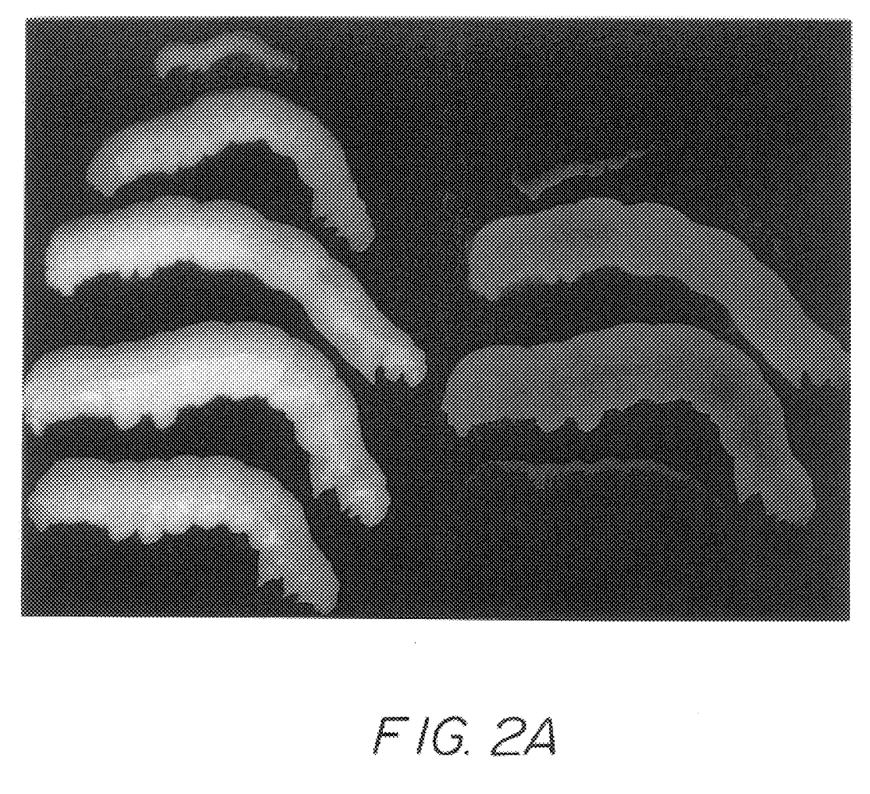
FIG. 2A Time course of larvae mass, total protein, and fluorescence intensity in baculovirus-infected insect larvae. Larvae were infected with the recombinant baculovirus vGFPuv of $5\times10^7$ pfu and grown at 30° C. Each data point represents three larvae; the data are reported on a per larva basis.
Figure 2B:
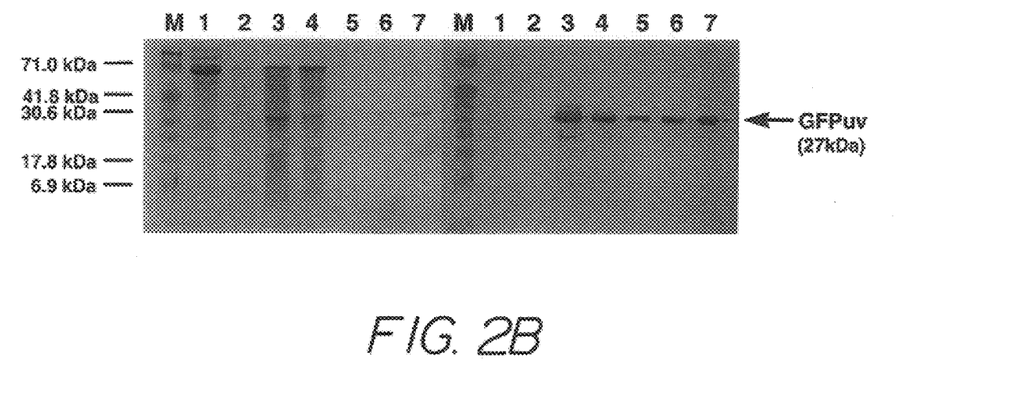
Figure 2C:
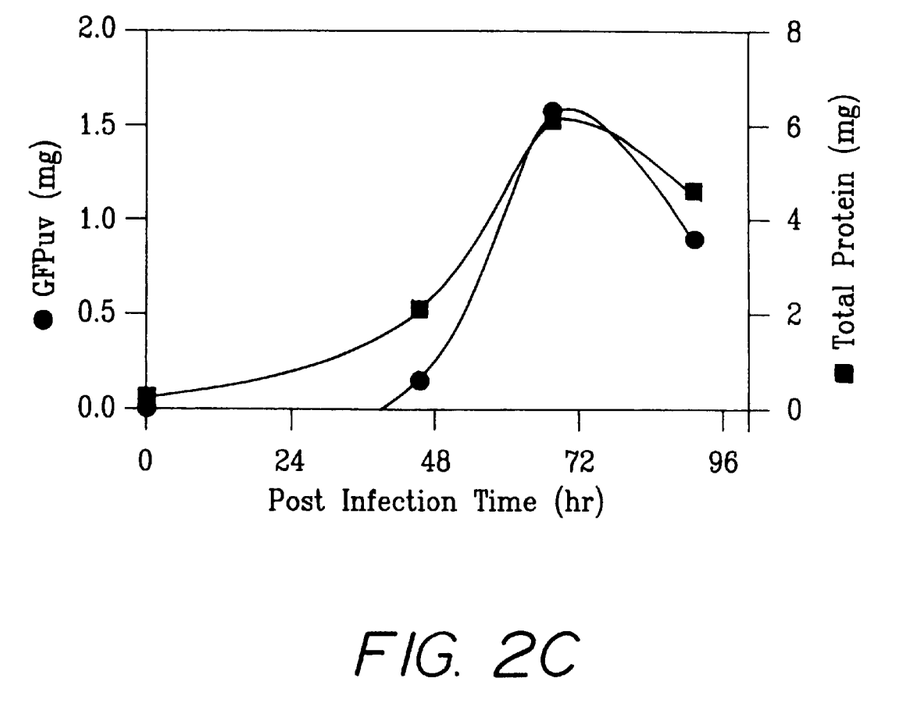
FIG. 2C Quantification of GFPuv in baculovirus-infected insect larvae (by densitometric scanning of Western blots).

GFPuv in baculovirus-infected insect larvae extracts was quantified as shown in FIG. 2. In FIG. 2(a), the larvae mass increased linearly throughout culture (4th instar), however, the total protein increased until 3 dpi (days post-infection), and then decreased. GFPuv fluorescence intensity, as measured in homogenized extracts, had roughly the same profile as total protein. Note, the fluorescence intensity was barely detectable in larvae until 2 dpi, but increased exponentially and was a maximum at 3 dpi, and then decreased by 56% until harvest. This decrease of GFPuv fluorescence intensity was related to the reduction of GFPuv mass due to proteolysis. Also, the decrease of total protein was due to the decrease in GFPuv, as discussed later.

SDS-PAGE and Western blot assays were used to evaluate the expression pattern of GFPuv (FIG. 2(b)). In the case of SDS-PAGE (left panel), two major bands appeared among many minor bands. The protein(s) of the upper right band are unknown, however, the lower band (27 kDa) was GFPuv as shown by the Western blot (right panel). In the case of uninfected insect larvae (lane 1), the GFPuv band was not seen in either the Western blot or SDS-PAGE. In the 3 dpi larvae (lane 3), the density of the GFPuv band was very thick on both gels, and a decrease in band density was observed in the 4 dpi larvae (lane 4). Notably, the decrease of fluorescence intensity after 3 dpi (56%) was not due to the formation of non-fluorescent protein but due to a decrease in the total GFPuv.

Quantification of GFPuv mass was then performed by densitometric scanning of Western blots, and a linear correlation with fluorescence intensity was obtained. The amounts of GFPuv and total protein during post-infection were depicted in FIG. 2(c). The GVPuv (mg/larva) profile was almost identical to the fluorescence intensity profile. The maximum amount of GFPuv was 1.58 per larva (6.87 mg/g larva mass), which was 26% of total protein. Interestingly, by simple mass balance, one-half of the decrease in total protein shown in FIG. 2(a) and noted earlier was due to the decrease in GFPuv. From these results, if a similar correlation between GFPuv mass and the mass of a GFP/product fusion protein were obtained, we could potentially estimate the quantity of fusion protein by simply detecting GFP fluorescence intensity.

Effects of Protease

In the Western blot of FIG. 2, we observed several bands below the 27 kDa GFPuv band, particularly, at 3 and 4 dpi (lanes 3 and 4). Even pure recombinant GFP (purified from E. coli by Clontech) had a small band at similar molecular weight (about 17 kDa) below the 27 kDa band (lanes 5 to 7). Since GFP is noted for its in vitro stability (Bokman and Ward, 1981; Inouye and Tsuji, 1994), these several small bands were likely proteolytically degraded GFPuv. Hence, the decrease of GFPuv observed after 3 dpi was likely due to degradation by proteases. Recall, the fluorescence intensity and quantified mass both decreased similarly during day 4. Interestingly, on the Western blot, both the degradation product and the principal GFP band decrease from day 3 to day 4.

Figure 3A:
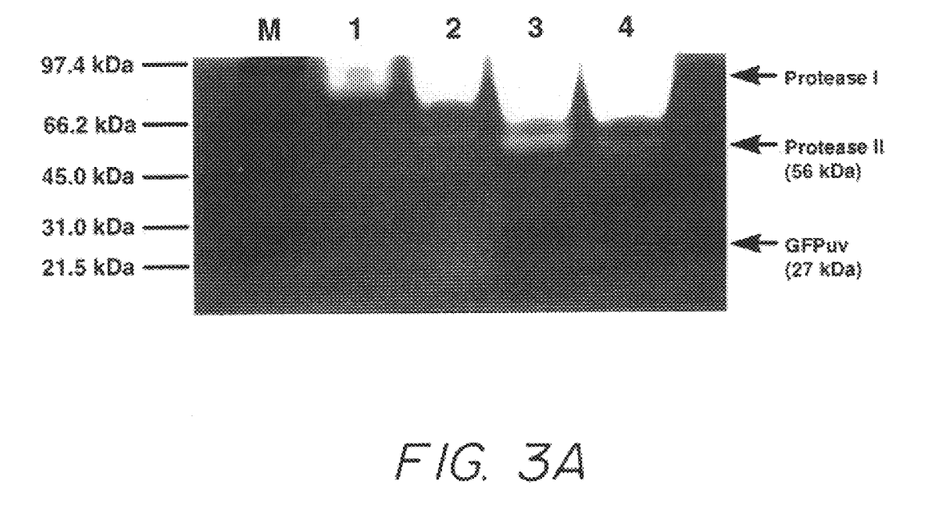
FIG. 3A SDS-GPAGE analysis of protease activity in larvae extracts. Molecular weight markers (lane M) are indicated on the left-hand side of the gel. Lane 1 is 0 day post-infection larvae, lane 2 is 2 day post-infection larvae, lane 3 is 3 day post-infection larvae, and lane 4 is 4 day post-infection larvae. The positions of protease I, protease II, and GFPuv are indicated on the right-hand side.
Figure 3B:
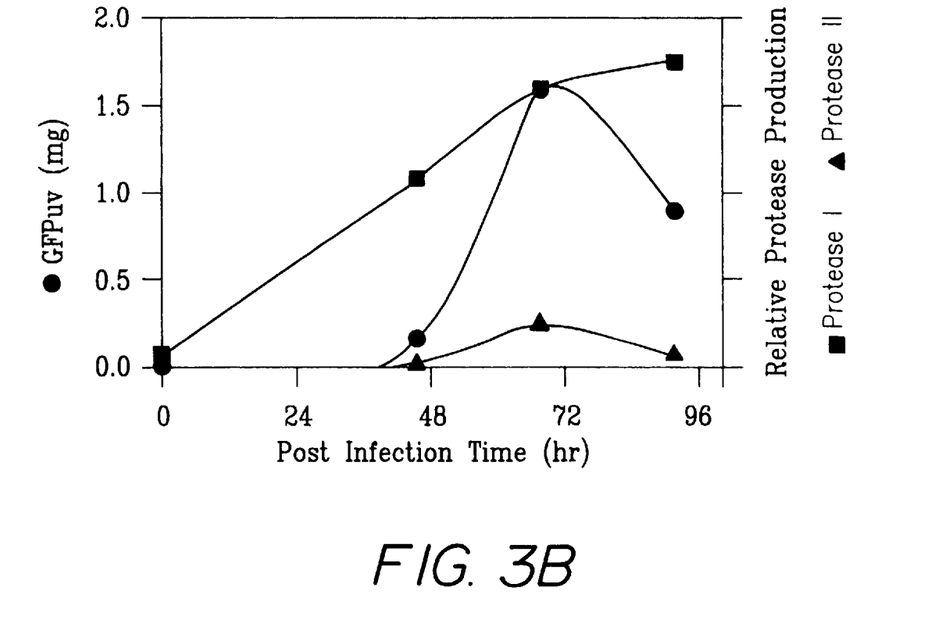
FIG. 3B Relative quantification of protease activity by densitometric scanning of SDS-GPAGE.

In order to examine in more detail the effect of protease on foreign production, SDS-G(gelatin)PAGE was performed as seen in FIG. 3(a). Proteolytic activity was evident as clear bands that appear on the otherwise dark blue gel. Two apparent proteases (one smear and one distinct band) appeared in baculovirus-infected insect larvae. For simplicity, the larger band at higher molecular weight was denoted protease I, and the smaller band was denoted protease II. Note that for protease I, because the activity was clearly prevalent during the electrophoresis resulting in a smear, we could hypothesize there was at least one protease at molecular weight indicated by the smear's lower edge (~65 kDa). Using densitometric scanning, relative quantification of each activity band was performed as shown in FIG. 3(b). Since the expression profile of protease I increased monotonically during the culture, we suspected this protease(s) was associated with larvae growth. Interestingly, on day 5 when the next instar began, protease I had completely disappeared (not shown). On the other hand, the expression profile of protease II (about 56 kDa) was almost same as the GFPuv expression profile. Therefore, it was thought this protease was virus-associated and was perhaps involved in the degradation of GFP or foreign protein. At present, only one protease (cathepsin L-like protease, 27.5 kDa, Slack et al., 1995) has been identified from AcNPV-infected insect cells. Additionally, a similar protease (~24 kDa) encoded by BmNPV has been implicated in recombinant protein degradation (Okhawa, et al., 1994). The protease activities we identified in the larvae were of significantly higher molecular weight (~56, and 65 kDa), suggesting they were unrelated. In another report from our lab, lower molecular weight proteases with papain-like activities were found from infected Sf-9 cell cultures (Naggie et al., 1997). Detailed characterization of this larval protease activity is underway.

Application of GFP for Foreign Protein Production

Figure 4:
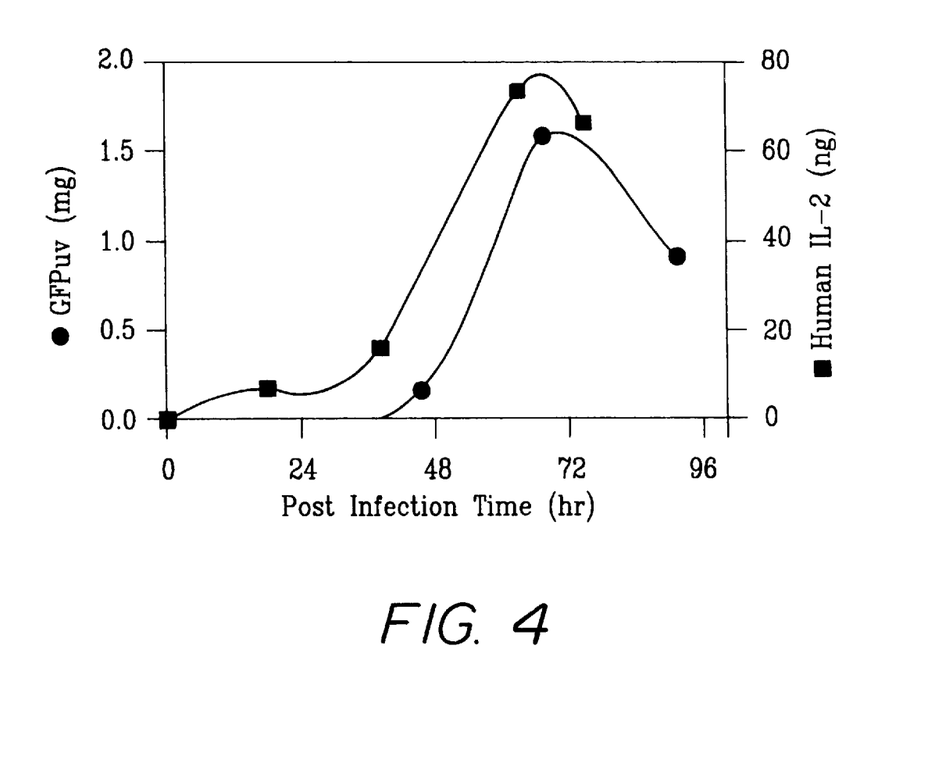
FIG. 4. Production profile of human IL-2 and GFPuv in baculovirus-infected insect larvae. The data are on a per larva basis, but each point represents 3 sacrificed larvae. In the case of IL-2, larvae were infected with the recombinant baculovirus vIL-2 of $7.5\times10^7$ pfu and grown at 30° C. Quantification of IL-2 was performed by ELISA.

In order to examine the feasibility of GFP as a marker for foreign protein production, the expression of human interleukin-2 (IL-2) was performed in baculovirus-infected insect larvae. IL-2 is the first of a series of lymphocytotrophic hormones (Gillis et al., 1978). Because of its role in tumor attacking lymphocyte proliferation, IL-2 is being evaluated as a therapeutic agent in the treatment of cancer (Rosenburg et al., 1984). Furthermore, IL-2 is used extensively as a tissue culture reagent due to its requirement for the survival of T-lymphocytes in culture. As shown in FIG. 4, the expression profile of human IL-2 was nearly identical to that of GFPuv. Until 2 dpi, IL-2 was not produced to any great extent, but then increased significantly to a maximum 3 dpi. Subsequently, IL-2 decreased by proteolysis. Our data were obtained from two recombinant baculoviruses infecting larvae independently under control of two different promoters (p10, for IL-2; polh, for GFP), yet the visualization of GFP coincided with the maximum in IL-2. Note that most baculovirus-expressed foreign proteins are placed under control of either of these two promoters, both are strong and nearly identically temporally regulated (Wang et al, 1996). Subsequently, we tested co-infection with both viruses simultaneously in the same larvae and there was a significant drop off in total recombinant protein yield (not shown).

In this example, we constructed a recombinant baculovirus for the expression of GFPuv in T. ni larvae and monitored the appearance and disappearance of GFPuv by visual observation, fluorescence intensity, SDS-PAGE, Western blot. The fluorescence intensity of GFPuv was linear with the mass of GFPuv. Disappearance in fluorescence intensity after 3 days post infection was due to proteolysis (as indicated by Western blot and SDS-GPAGE). GFPuv was visualized in larvae having large opaque carcasses (~30 mm). The optimal harvest time was realized without sacrificing the larvae by simply placing them on a UV transilluminator table and visualizing the brightness of green fluorescence. We obtained a nearly identical expression profile of human IL-2 in baculovirus-infected T. ni larvae, demonstrating robustness of the expression system under two different promoters. At present, these results simplify the existing IL-2 production process in that a fraction of the larvae could be infected with vGFPuv in parallel to those infected with the product baculovirus so that variations in temperature, humidity, crowding, etc., would be accounted for in the synchronous process and the maximum protein obtained at the point of highest green light intensity.

While particular embodiments of the invention have been described in detail, it will be apparent to those skilled in the art that those embodiments are exemplary rather than limiting. Numerous modifications and variations of the present invention are possible in light of the above disclosure and therefore, within the scope of the appended claims.

REFERENCES CITED THROUGHOUT THE INSECT PROTEIN MANUFACTURING PATENT APPLICATION

Bokman, S. H., Ward, W. W. 1981. Renaturation of Aequorea green-fluorescent protein. Biochem. Biophys. Res. Comm. 101: 1372–1380.

Cha, H. J., Pham, M. Q., Rao, G., Bentley, W. E. 1997. Expression of Green Fluorescent Protein in Insect Larvae and Its Application for Heterologous Protein Production, accepted in Biotechnology and Bioengineering.

Chalfie, M., Tu, Y., Euskirchen, G., Ward, W. W., Prasher, D. C. 1994. Green fluorescent protein as a marker for gene expression. Science 263: 802–805.

Crameri, A., Whitehorn, E. A., Tate, E., Stemmer, W. P. C. 1996. Improved green fluorescent protein by molecular evolution using DNA shuffling. Nature Biotechnol. 14: 315–319.

Davis, T. R., and H. A. Wood, 1995. Intrinsic Glycosylation Potentials of Insect Cell Cultures and Insect Larvae, In vitro cellular & developmental biology journal. 31:659.

Gillis, S., Ferm, M. M., Ou, W., Smith, K. A. 1978. T cell growth factor: parameters of production and a quantitative microassay for activity. J. Immunol. 120: 2027–2032.

Harcum, S. W., Bentley, W. E. 1993. Detection, quantification, and characterization of protease in recombinant *Escherichia coli*. Biotechnol. Techniques 7: 441–447.

Heinlein, M., Epel, B. L., Padgett, H. S., Beachy, R. N. 1995. Interaction of tobamovirus movement proteins with the plant cytoskeleton. Science 270: 1983–1985.

Ikawa, M., Kominami, K., Yoshimura, Y., Tanaka, K., Nishimune, Y., Okabe, M. 1995. Green fluorescent protein as a marker in transgenic mice. Devel. Growth. Differ. 37: 455–459.

Inouye, S., Tsuji, F. I. 1994. Aequorea green fluorescent protein: expression of the gene and fluorescent characteristics of the recombinant protein. FEBS Letters 341: 277–280.

Johnson, F. H., Shimomura, O., Saiga, Y., Gershman, L. C., Reynolds, G. T., Waters, J. R. 1962. Quantum efficiency of Cypridina luminescence, with a note on that of Aequorea. J. Cell. Comp. Physiol. 60: 85–103.

Kain, S. R., Adams, M., Kondepudi, A., Yang, T. T., Ward, W. W., Kitts, P. 1995) The green fluorescent protein as a reporter of gene expression and protein localization. BioTechniques 17: 982–987.

Kashima et al., 1985. Unique Structure of Murine IL-2 as Deduced from Cloned cDNA. Nature 313: 402.

Maeda, S., Kawai, T., Obinata, M., Fujiwara, H., Horiuchi, T., Saeki, Y., Sato, Y., Furusawa, M. 1985. Production of human α-interferon in silkworm using a baculovirus vector. Nature 315: 592–594.

Marumoto, Y., Sato, Y., Fujiwara, H., Sakano, K., Sakei, Y., Agata, M., Furusawa, M., Maeda, S. 1987. Hyperproduction of polyhedrin-IGF II fusion protein in silkworm larvae infected with recombinant *Bombyx mori* nuclear polyhedrus virus. J. Gen. Virol. 68: 2599–2606.

Miyajima, A., Schreurs, J., Otsu, K., Kondo, A., Arai, K., Maeda, S. 1987. Use of silkworm, *Bombyx mori,* and an insect baculovirus vector for high-level expression and secretion of biologically active mouse interleukin-3. Gene 58: 273–281, Medin, J. A., Hung, L., Gathy, K., Evans, R. K., Coleman, M. S. 1990. Efficient, low-cost protein factories: expression of human adenosine deaminase in baculovirus-infected insect larvae. Proc. Nat. Acad. Sci. USA 87: 2760–2764.

Naggie, S., Pulliam, T. R., Bentley, W. E. 1996. Elicitation of protease activity in insect (Sf-9) cell culture. Abstracts of the American Chemical Society 211: 163.

Niedz, R. P., Sussman, M. R., Satterlee, J. S. 1995. Green fluorescent protein: an in vivo reporter of plant gene expression. Plant Cell Reports 14: 403–406.

Ohkawa, T. K., Majima, S. Maeda. 1994. A cystein protease encoded by the baculovirus *Bombyx mori* nuclear polyhedrosis virus. J. Virol. 68: 6619–6625.

Page, A. P., and R. M. Maizels. Biosynthesis and glycosylation of serine/threonine-rich secreted proteins from *Toxocara canis* larvae, Parasitology, 1992, 105:297.

Palhan, V. B., Sumathy, S., Gopinathan, K. P. 1995. Baculovirus mediated high-level expression of luciferase in silkworm cells and larvae. BioTechniques 19: 97–104.

Pham, M. Q., Wier, M., Cha, H. J., Bentley, W. E. 1997. Human Interleukin-2 Production in Insect (*Trichoplusia ni*) Larvae: The Effects and Partial Control of Proteolysis, submitted in Biotechnology and Bioengineering.

Pines, J. 1995. GFP in mammalian cells. Trends Genet. 11: 326–327.

Prasher, D. C., Eckenrode, V. K., Ward, W. W., Prendergast, F. G., Cormier, M. J. 1992. Primary structure of the *Aequorea victoria* green fluorescent protein. Gene 111: 229–233.

Reilander, H., Haase, W., Maul, G. 1996, Functional expression of the *Aequorea victoria* green fluorescent protein in insect cells using the baculovirus expression system. Biochem. Biophys. Res. Commun. 219: 14–20.

Schlenstedt, G., Saavedra, C., Loeb, J. D. J., Cole, C. N., Silver, P. A. 1995. The GFP-bound form of the yeast Ran/TC4 homologue blocks nuclear protein import and appearance of poly(a)+RNA in the cytoplasm. Proc. Natl. Acad. Sci. USA 92: 225–229.

Shimomura, O., Johnson, F. H., Saiga, Y. 1962. Excitation, purification and properties of aequorin, a bioluminescent protein from the luminous hydromedusan. Aequorea. J. Cell. Comp. Physiol. 59: 223–227.

Slack, J. M., J. Kuzio, P. Falkner. 1995. Characterization of n-cath, a cathepsin L-like proteinase expressed by the baculovirus *Autographa californica* nuclear polyhedrosis virus. J. Gen. Virol. 76: 1091–1098.

Stearns, T. 1995. The green revolution. Current Bio. 5:262–264

Tamiguchi et al. 1983. Structure and Expression of Cloned cDNA for Human IL-2. Nature 302:305.

Tanada, Y. (1989). In *Invertebrate Cell System Applications.* Vol. 2 (ed. Mitsuhashi). CRC Press, Boca Raton, Fla., pp. 43–49.

U.S. Pat. No. 5,472,858: Production of Recombinant Proteins in Insect Larvae.

Van Den Heuvel, J. M., et al. Wu, G.-I., Zou, D.-J., Koothan, T., Cline, H. T. 1995. Infection of frog neurons with vaccinia virus permits in vivo expression of foreign proteins. Neuron 14:681–684.

What is claimed is:

1. A continuous process for the production of a protein of interest in insect larvae, comprising the steps of:
   a) providing an infected insect larvae food which comprises adding a baculovirus vector to insect larvae food, wherein said baculovirus vector comprises a DNA encoding the protein of interest operatively linked to a gene encoding a green fluorescent protein (GFP) or a GFP mutant, thereby providing a composition of infected insect larvae food;
   b) continuously infecting insect larvae by feeding said larvae the infected insect larvae food of step (a), thereby resulting in a population of infected insect larvae;
   c) cultivating the infected insect larvae population of step (b) under suitable conditions for the expression of the protein of interest and the GFP or the GFP mutant by the infected insect larvae population;

d) monitoring the infected insect larvae population for the expression of the protein of interest and the GFP or the GFP mutant by measuring the intensity of the fluorescence of GFP or the GFP mutant;

e) correlating the intensity of the fluorescence of GFP or the GFP mutant with the amount of the protein of interest expressed;

f) harvesting the larvae which express the protein of interest from the population of infected insect larvae;

g) recovering the protein of interest from the harvested larvae.

2. The process of claim 1, wherein said GFP is GFPuv which has spectral properties that enable quantitation of the protein of interest using fluorescence.

3. The process of claim 1, wherein the protein of interest is expressed as a fusion protein with the GFP or the GFP mutant.

4. The process of claim 1, wherein step (a) comprises adding 500 µl baculovirus vector loading to insect larvae food, wherein said baculovirus vector loading comprises at least $5 \times 10^7$ pfu/ml.

5. The process of claim 1, wherein the insect larvae are of the species *Trichoplusia ni*.

6. The process of claim 5, wherein the insect larvae are in the fourth instar.

7. The process of claim 1, wherein the DNA encoding the protein of interest and the GFP or the GFP mutant comprise a nucleic acid sequence which encodes an amino acid sequence, wherein said amino acid sequence is cleavable by a specific enzyme which allows the expressed protein of interest to be cleaved off from the GFP or the GFP mutant.

8. The process of claim 7, wherein the specific enzyme is enterokinase.

9. The process of claim 8, wherein the GFP or the GFP mutant comprises a His-affinity tail.

10. The process of claim 9, wherein the protein of interest is interleukin-2.

11. The process of claim 1, wherein the infected insect larvae expressing the protein of interest are harvested at least 3–5 days post infection.

12. The process of claim 1, wherein the infected insect larvae expressing the protein of interest are harvested at least four days post infection.

13. The process of claim 1, wherein the harvested larvae are preserved at a pH of about 3.5 to 4.0.

14. The process of claim 13, wherein the harvested larvae are preserved in the presence of protease inhibitors selected from the group consisting of EDTA, PMSF, benzamidine and mixtures thereof.

15. A continuous process for the production of interleukin-2 in insect larvae, comprising the steps of:

a) providing infected insect larvae food which comprises adding a baculovirus vector to insect larvae food, wherein said baculovirus vector comprises a DNA encoding interleukin-2 operatively linked to a gene encoding a green fluorescent protein (GFP) or a GFP mutant, thereby providing a composition of infected insect larvae food;

b) continuously infecting insect larvae by feeding said larvae the infected insect larvae food of step (a), thereby resulting in a population of infected insect larvae;

c) cultivating the infected insect larvae population of step (b) under suitable conditions for the expression of interleukin-2 and the GFP or the GFP mutant by the infected insect larvae population;

d) monitoring the infected insect larvae population for the expression of interleukin-2 and the GFP or the GFP mutant by measuring the intensity of the fluorescence of GFP or the GFP mutant;

e) correlating the intensity of the fluorescence of GFP or the GFP mutant with the amount of interleukin-2 expressed;

f) harvesting the larvae which express interleukin-2 from the population of infected insect larvae;

g) recovering interleukin-2 from the harvested larvae.

16. The process of claim 15, wherein the infected insect larvae expressing interleukin-2 are harvested at least 3–5 days post infection.

17. The process of claim 15, wherein the harvested larvae are preserved in the presence of protease inhibitors selected from the group consisting of EDTA, PMSF, benzamidine and mixtures thereof.

* * * * *